United States Patent
Chang et al.

(12)

(10) Patent No.: US 6,881,726 B2
(45) Date of Patent: Apr. 19, 2005

(54) AQUEOUS COMPOSITIONS CONTAINING METRONIDAZOLE

(75) Inventors: Yunik Chang, Sonoma, CA (US); Gordon J. Dow, Santa Rosa, CA (US)

(73) Assignee: Dow Pharmaceutical Sciences, Petaluma, CA (US)

(*) Notice: Subject to any disclaimer, the term of this patent is extended or adjusted under 35 U.S.C. 154(b) by 59 days.

(21) Appl. No.: 10/033,835

(22) Filed: Dec. 24, 2001

(65) Prior Publication Data

US 2003/0119783 A1 Jun. 26, 2003

(51) Int. Cl.[7] .................. A61K 31/724; A61K 31/40
(52) U.S. Cl. ............................. 514/58; 514/398
(58) Field of Search ................... 514/58, 398

(56) References Cited

U.S. PATENT DOCUMENTS 6,468,989 B1 * 10/2002 Chang et al. .................. 514/58

FOREIGN PATENT DOCUMENTS

WO    WO 99/09988    * 3/1999

OTHER PUBLICATIONS

Redenti, E. et al "Drug/cyclodextrin/hydroxy acide multi-component systems" J. Pharm. Sci. (2000) vol. 89, No 1, pp. 1–8.*

* cited by examiner

*Primary Examiner*—James O. Wilson
*Assistant Examiner*—Leigh C. Maier
(74) *Attorney, Agent, or Firm*—Howard Eisenberg, Esq.

(57) ABSTRACT

An aqueous solution of metronidazole in which the concentration of metronidazole is higher than 0.75%. The solution contains a combination of solubility-enhancing agents, one of which is a cyclodextrin such as beta-cyclodextrin and the second is a compound other than a cyclodextrin. Methods of manufacture and therapeutic use of the solution are disclosed.

50 Claims, 1 Drawing Sheet

AQUEOUS COMPOSITIONS CONTAINING METRONIDAZOLE

The invention pertains to the field of topically applied medications for treatment of skin and mucosal disorders. In particular, the invention pertains to aqueous compositions containing metronidazole as the active ingredient.

BACKGROUND OF THE INVENTION

Metronidazole, 1-(2-hydroxyethyl)-2-methyl-5-nitroimidazole, has long been known as an effective drug to treat a variety of disorders, and is especially well known for the treatment of various protozoal diseases. As a topical therapy, metronidazole has also been shown to be useful in treating various skin disorders, including acne rosacea, bacterial ulcers, and perioral dermatitis. See, Borgman, U.S. Pat. No. 4,837,378. Metronidazole has been found to have an anti-inflammatory activity when used topically to treat dermatologic disorders. See, Czernielewski, et al., U.S. Pat. No. 5,849,776. Metronidazole may also be used as an intravaginal therapeutic agent for the treatment of bacterial vaginosis. See, Borgman, U.S. Pat. No. 5,536,743.

Compositions containing metronidazole for treatment of dermatologic disorders are available in cream, lotion and gel forms. One commercially available metronidazole cream product, NORITATE™ (Dermik Laboratories, Inc., Collegeville, Pa. 19426 USA) contains 1% metronidazole in which the insoluble drug is suspended in the opaque cream. A commercially available metronidazole gel product, METROGEL® (Galderma Laboratories, Inc. Fort Worth, Tex., 76133 USA), contains 0.75% metronidazole which is solubilized to produce a clear gel.

For the treatment of many dermatologic and mucosal disorders, it is often preferable to use a solubilized water-based formulation, such as a gel, rather than a cream, lotion or an ointment. Creams, lotions (typically oil in water emulsions) and ointments (typically petroleum jelly based compositions) are often comedogenic, acnegenic, or not cosmetically appealing to patients. Solubilized topical products are generally more bioavailable than products in which the active ingredient is insoluble.

The oil-based cream and ointment metronidazole formulations have an advantage over presently available gel-based formulations in that oil-based formulations may contain a concentration of metronidazole of 1%. Aqueous-based gel compositions are limited to a concentration of metronidazole of 0.75% because of the poor solubility of metronidazole in water.

Cyclodextrins have been shown to enhance the solubility of various drugs in aqueous solutions. An amphiphilic or lipophilic drug, such as metronidazole, is partially or completely enclosed within this cage structure, thereby increasing the solubility of the drug in aqueous media. Cyclodextrins have certain disadvantages, however, including expense, limitations of cyclodextrin solubility, incompatibility in certain vehicles, and potential for local and systemic toxicity.

Several authors have described the use of beta-cyclodextrin (BCD) in combination with metronidazole. Kata and Antal, Acta Pharmaceutica Hungarica, 54:116–122 (1984), disclose a marked increase in the rate of dissolution of metronidazole when dissolved in a solution containing BCD at 37° C. The stability of the BCD/metronidazole solutions is not addressed. Major problems with the use of BCD to solubilize drugs such as metronidazole is that BCD has a relatively low solubility in water and is a relatively inefficient solubilizer, particularly for lipophilic or amphiphilic drugs such as metronidazole. Additionally, cyclodextrins, such as BCD and its derivatives, are expensive and the drug formulations containing BCD as a solubilizing agent likewise become expensive. A need exists for a way to increase the solubility of drugs which requires a reduced concentration of BCD.

Solubility enhancing agents other than cyclodextrins have been described. Yie W. Chien, Journal of Parenteral Science and Technology, 38(1):32–36 (January 1984), discloses that niacinamide is a solubility enhancing agent that can increase the water solubility of MTZ. Chien further discloses that the water soluble vitamins ascorbic acid, and pyridoxine are solubility enhancing agents for aqueous solutions. Chien discloses that the solubility of metronidazole in water increases linearly with relation to the concentration of these water soluble vitamins in the solution. The Chien article is incorporated herein by reference. The prior art does not address the combination of cyclodextrins, such as BCD, with other solubility enhancing agents, such as niacinamide or other water soluble vitamins.

SUMMARY OF THE INVENTION

It has been surprisingly discovered that the combination of a cyclodextrin and a second solubility enhancing agent, such as niacinamide or niacin, has a synergistic effect on the aqueous solubility of amphiphilic or lipophilic chemical compounds such as metronidazole. The second solubility enhancing agent may be other than niacinamide or niacin. The synergistic effect provided by the combination of cyclodextrin and the second solubility enhancing agent permits the use of lower concentrations of cyclodextrins than would be necessary to obtain a desired level of solubility of the chemical compound in the absence of the second solubility enhancing agent. Because cyclodextrins are expensive, has limited aqueous solubility, and is not entirely free of toxicity, the invention provides an important way to greatly reduce costs in the formulation and preparation of pharmaceutical preparations, as well as to increase the solubilizing capability of cyclodextrins such as BCD, and to obtain desired concentrations of pharmacologic compounds while minimizing the amount of cyclodextrins used.

As used herein, the term "solubility enhancing agent" or "solubility enhancer" means a chemical compound that, when present in solution in a solvent, increases the solubility of a second chemical compound, such as an active ingredient, in the solvent, but which chemical compound is not itself a solvent for the second chemical compound.

All concentrations referred to in this specification are % w/w, unless indicated otherwise.

The invention is described below with reference to a particular cyclodextrin, BCD, and a particular chemical compound, metronidazole. It is conceived, however, that the invention is applicable to other cyclodextrins, both crystalline and non-crystalline, including alpha and gamma cyclodextrins, and crystalline and non-crystalline derivatives thereof, and other amphiphilic and lipophilic chemical compounds besides metronidazole.

Physically stable aqueous solutions of higher than 0.75% metronidazole (MTZ) may be obtained by combining in the solution a first solubility enhancing agent which is a cyclodextrin, such as beta-cyclodextrin (BCD), and a second solubility enhancing agent, such as niacinamide or niacin. The combination of the cyclodextrin and the second solubility enhancing agent provides a synergistic effect in increasing the solubility of MTZ in water. These discoveries permit the production of aqueous MTZ solutions, including solutions that are gels, at levels of 1% MTZ or higher. At such levels, MTZ may be effectively used as a topical medicament.

In one embodiment, the invention is an aqueous solution having a concentration of MTZ higher than 0.75% w/w, preferably about 1% or higher. The aqueous solution contains a cyclodextrin, such as BCD, as a first solubility enhancing agent and a second solubility enhancing agent, such as niacin or niacinamide. Preferably, the level of each of the cyclodextrin and the second solubility enhancing agent is less than that which, in the absence of the other solubility enhancing agent, would provide for a dissolved concentration of the MTZ to the level of that present in the aqueous solution. If desired, however, the solution may contain an excess of the second solubility enhancing agent. Most preferably, the enhanced solubility of MTZ in the combination solution is higher than the sum of the enhanced solubilities of MTZ in two solutions, each of which contains a single solubility enhancer at the concentration present in the combination solution. Preferably, the solution is substantially free of aqueous solubility-enhancing agents other than a cyclodextrin and the second solubility enhancing agent. Preferably, the solution is an aqueous gel.

In another embodiment, the invention is a method for the manufacture of an aqueous solution of MTZ having a concentration greater than 0.75%, preferably about 1.0% or higher. The method includes combining MTZ and two solubility enhancing agents, one of which is a cyclodextrin such as BCD, in a water based solution wherein the concentration of the final aqueous solution of MTZ is higher than 0.75%. Preferably, the level of each of the cyclodextrin and the second solubility enhancing agent is less than that which, in the absence of the other solubility enhancing agent, would provide for a dissolved concentration of the MTZ to the level of that present in the aqueous solution. If desired, however, an excess of the second solubility enhancing agent may be used. Most preferably, the enhanced solubility of MTZ in the combination solution is higher than the sum of the enhanced solubilities of MTZ in two solutions, each of which contains a single solubility enhancer at the concentration present in the combination solution. Preferably, a gelling agent is further combined in the solution, preferably after addition of the MTZ and the solubility-enhancing agents.

In another embodiment, the invention is a method for the treatment of a dermatologic or mucosal disorder. The method includes topically applying to affected areas an aqueous solution of MTZ and a cyclodextrin, such as BCD, and a second solubility enhancing agent, such as niacin or niacinamide., which solution has a concentration of MTZ higher than 0.75%, preferably about 1.0% or higher. Preferably, the level of each of the cyclodextrin and the second solubility enhancing agent is less than that which, in the absence of the other solubility enhancing agent, would provide for a dissolved concentration of the MTZ to the level of that present in the aqueous solution. If desired, however, the solution may contain an excess of the second solubility enhancing agent. Most preferably, the enhanced solubility of MTZ in the combination solution is higher than the sum of the enhanced solubilities of MTZ in two solutions, each of which contains a single solubility enhancer at the concentration present in the combination solution. Preferably, the aqueous solution is a gel.

In another embodiment, the invention is a kit for the treatment of a dermatologic or mucosal disorder. The kit of the invention includes a container that contains an aqueous solution of MTZ and which aqueous solution contains a first solubility enhancing agent which is a cyclodextrin, such as BCD, and a second solubility enhancing agent such as niacin or niacinamide. Preferably, the level of each of the cyclodextrin and the second solubility enhancing agent is less than that which, in the absence of the other solubility enhancing agent, would provide for a dissolved concentration of the MTZ to the level of that present in the aqueous solution. If desired, however, the solution may contain an excess of the second solubility enhancing agent. Most preferably, the enhanced solubility of MTZ in the combination solution is higher than the sum of the enhanced solubilities of MTZ in two solutions, each of which contains a single solubility enhancer at the concentration present in the combination solution. Preferably, the aqueous solution is a gel.

DETAILED DESCRIPTION OF THE INVENTION

Figure 1:
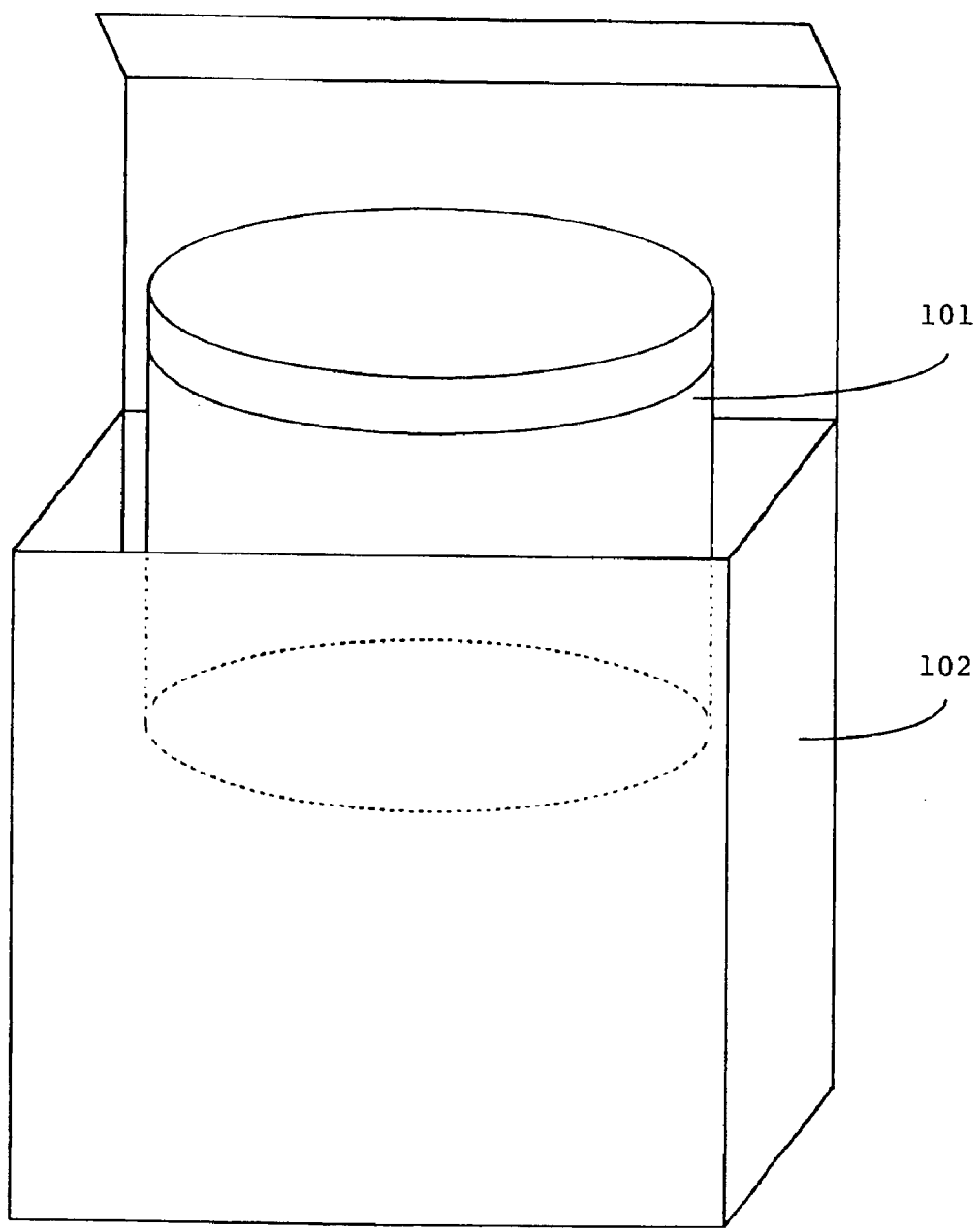
FIG. 1 shows a diagrammatic representation of a preferred embodiment of the kit of the invention.

It has been unexpectedly discovered that stable aqueous solutions of metronidazole (MTZ) of greater than 0.75% w/w, and even about 1.0% or higher, are able to be obtained by using a combination of solubility-enhancing agents, wherein one of the solubility enhancing agents is a cyclodextrin, such as BCD, and the second solubility enhancing agent is other than a cyclodextrin. Examples of suitable second enhancing agents include niacin and niacinamide.

As used in this specification, the term "stable" refers to physical, rather than chemical, stability. In accordance with the invention, the metronidazole solutions of the invention are physically stable, that is substantially no crystal or precipitate from solution, when stored at refrigerated temperatures of 5° C. for at least 7 days.

The physically stable aqueous solutions of metronidazole at concentrations greater than 0.75% are obtained without the substantial presence of water-miscible organic solvents, such as ethyl alcohol or propylene glycol, which may be irritating to intact or damaged skin or mucosal surfaces. The elimination of these organic solvents provides a therapeutic solution that has decreased potential for irritation and makes the solutions especially good for treating topical dermatologic conditions, such as rosacea, that may be worsened by irritating chemicals present in a therapeutic formulation. However, if desired, such organic solvents may be included in the solution, up to a concentration of about 10%. In a most preferred embodiment, the aqueous solutions are substantially free of organic solvents for MTZ.

The stable aqueous MTZ solutions of the invention have a concentration of MTZ greater than 0.75% w/w. Preferably, the concentration of MTZ in the solution of the invention is about 1.0%. In accordance with the invention, the concentration of MTZ in aqueous solution may be even higher, such as 1.25%, 1.5%, 2.0%, or 2.5%, or more. At a level of 1% or higher of MTZ, the aqueous solution may be effectively used therapeutically as a topical formulation.

The solution is preferably in the form of a gel. Therefore, the aqueous MTZ solution preferably contains a gelling agent. Any gelling agent that is water-dispersible and forms an aqueous gel of substantially uniform consistency is suitable for use in the solution of the invention so long as the gelling agent does not substantially interfere with the water solubility of MTZ or with the therapeutic efficacy of the solution. "Substantially interfere" means that the inclusion of the gelling agent decreases the solubility of MTZ to 0.75% w/w or less in aqueous solution. A preferred gelling agent is hydroxyethylcellulose (NATROSOL™, Hercules Inc., Wilmington, Del., USA). Examples of other suitable gelling agents include carboxyvinyl polymers, such as CARBOPOL® 934, 940, and 941 (Noveon, Inc., Akron, Ohio, USA).

The level of the cyclodextrin in the solution may be varied depending upon the desired dissolved concentration of MTZ. In general, it is preferable to use as low a concentration of cyclodextrin as possible to obtain the desired concentration of MTZ because cyclodextrins are expensive, of limited aqueous solubility, not entirely free of toxicity, and the presence of cyclodextrin may be irritating to certain intact and diseased skin and mucosal surfaces. In accordance with the invention, the concentration of cyclodextrin in aqueous solution may be between 0.1% and 20%, or higher. Preferably, the concentration of cyclodextrin in the solution is no more than about 5% w/w. In the case of beta-cyclodextrin, the concentration in aqueous solution is limited by its solubility in water. An aqueous solution, such as a gel, of beta-cyclodextrin is saturated at a concentration of about 0.5% at 5° C. (refrigerator temperature).

The solutions, especially in gel formulation, are non-tacky, fast-drying, and cosmetically elegant. The solutions, including the gel formulations, are physically stable at 5° C. (refrigerator temperature) or room temperature conditions for at least 7 days. No crystal formation or precipitation is observed after one week at 5° C.

It is preferred that the aqueous solution of the invention be substantially free of pharmacologically active compounds other than MTZ having a water-solubility which is increased by the presence of cyclodextrins. These other compounds may act as competitors for the sequestration sites within the cyclodextrin cage structure and reduce the MTZ solubility enhancement by the cyclodextrin. Multiple solutes that are increased in solubility by cyclodextrins may be utilized in the solutions so long as the level of cyclodextrin and the second solubility enhancer in the solution is sufficiently high to result in the desired dissolved concentration of MTZ, even in the presence of the competitor solute.

In a preferred embodiment of the invention, the amount of cyclodextrin in the solution is at a level below that which enhances the solubilization of MTZ to the level desired, and a second solubility enhancer, such as niacinamide or niacin, is included in the solution at a level that permits the desired concentration of MTZ in aqueous solution to be attained. For example, if a stable 1% MTZ aqueous solution is desired, 0.1% to 1.0% BCD may be used and an amount of niacinamide or niacin may be combined in the solution to bring the solubility of MTZ to 1%. The amount of niacinamide to be combined in the solution is less than that which, without the presence of BCD in the solution, can enhance the solubility of MTZ sufficiently to obtain a 1% solution of MTZ, or whatever level of MTZ is desired. In accordance with this embodiment of the invention for a 1% aqueous solution of MTZ, the concentration of BCD % w/w in the solution is preferably at a level of 1.0% or less and the concentration of niacinamide or niacin equal to or more than that of BCD.

The aqueous solutions, including the aqueous gels, of the invention may be made in any way that results in a stable MTZ concentration of greater than 0.75%, preferably of 1.0% or higher. Preferably, the solubility enhancers and the MTZ are combined in water, or a water-based solution, before the addition of a gelling agent, or at least before gelling of the solution occurs. Preferably, the solubility enhancers are dissolved in water before addition of the MTZ.

In a preferred method of manufacture of the aqueous solution of the invention, an aqueous solution of BCD and niacinamide or niacin is prepared, wherein the levels of BCD and niacinamide or niacin are as described above. Metronidazole is then added to the solution. The amount of metronidazole added to the solution may be an amount calculated to provide the desired concentration of MTZ or it may be an excess amount of MTZ. The solution is preferably stirred or agitated at an elevated temperature and then permitted to cool to room or refrigerator temperature. A gelling agent, if desired, is preferably added at any time after the addition of MTZ to the solution. Most preferably, the gelling agent is added to the solution after the agitation of the solution, during the cooling of the solution, or following cooling of the solution.

The solutions of the invention, including gels, may be used for the topical treatment of dermatologic or mucosal disorders that are responsive to therapy with metronidazole. In accordance with the method of treatment of the invention, a stable aqueous solution containing metronidazole at a concentration higher than 0.75% w/w, preferably about 1% or higher, is topically applied to skin or mucosal surfaces in need of such therapy. The applied solution preferably contains a cyclodextrin like BCD, as described above, in combination with niacin or niacinamide, as described above.

The therapeutic method of the invention may be used to treat any disorder that is responsive, or potentially responsive, to metronidazole therapy. Examples of disorders that are suitably treated in accordance with the invention include inflammatory lesions on the skin, oral mucosa, or vaginal mucosa, diabetic foot ulcers, and certain infectious diseases that may be treated topically. In a preferred embodiment, the method of the invention is used to treat rosacea.

At concentrations of about 1% or higher, the application of the metronidazole solution is preferably only once daily. The solution is applied on a daily basis, one or more times per day, for a time sufficient to produce an amelioration or a cure of the disorder. In certain chronic disorders, the solution may be applied one or more times daily for a prolonged period to prevent worsening of the disorder.

In another embodiment of the invention, a kit (FIG. 1) is provided for the topical treatment of skin or mucosal disorders. The kit contains a jar 101 or other container suitable for holding an aqueous metronidazole solution as described herein, and instructions (not illustrated) for applying the solution topically to affected areas of the skin or mucosal surface. Preferably, the metronidazole solution has a concentration of metronidazole of about 1% or higher and the instructions call for applying the metronidazole solution to affected areas once daily. The jar 101 is preferably packaged within a box 102, upon which additional information, such as instructions, may be written.

The following non-limiting examples provide a further description of the invention.

EXAMPLE 1

All solutions in the following examples contain the components listed as the generic formula or gel vehicle shown in Table 1.

TABLE 1

| COMPONENT | % w/w |
|---|---|
| Methylparaben | 0.15 |
| Propylparaben | 0.05 |
| Phenoxethanol | 0.7 |
| Edetate sodium | 0.05 |
| Hydroxyethyl cellulose (HEC) | 1.25 |
| Beta-cyclodextrin (BCD) | As shown in Tables 2 to 6 |
| Niacinamide or Niacin | As shown in Tables 2 to 6 |
| Purified Water | QS 100.00 |

Different solutions according to Table 1 were made with varying concentrations of beta-cyclodextrin (BCD). The solutions of BCD were maintained at 5° C. monitored weekly for two weeks for signs of crystal or precipitate formation. The results are shown in Table 2. The data show that the saturated BCD solubility in the aqueous solutions at 5° C. is about 0.5%.

TABLE 2

| BCD % w/w | Results after storage at 5° C. |
|---|---|
| 0.5 | Clear after 2 weeks |
| 0.6 | Crystals formed after 2 weeks |
| 0.7 | Crystals at one week |
| 0.9 | Crystals at one week |
| 1.0 | Crystals at one week |
| 1.2 | Crystals at one week |
| 1.4 | Crystals at one week |
| 1.5 | Crystals at one week |

EXAMPLE 2

Different concentrations of metronidazole were prepared with the gel vehicle of Example 1 containing 0.5% BCD. The metronidazole (MTZ)/BCD solutions were maintained at 5° C. for one week. The results are shown in Table 3.

TABLE 3

| BCD % w/w | MTZ % w/w | Result at 5° C., 1 week |
|---|---|---|
| 0.5 | 0.9 | Crystals formed |
| 0.5 | 0.8 | Clear |
| 0.5 | 0.7 | Clear |

From this study, the stable solubility of metronidazole in the gel vehicle containing 0.5% BCD at 5° C. was determined to be about 0.8% w/w.

EXAMPLE 3

A similar study using various concentrations of niacinamide showed that the concentration of niacinamide required to obtain a stable aqueous gel solution of 1.0% metronidazole is about 3%. Various gel solutions of Table 1 were prepared with a concentration of 1.0% metronidazole and containing either 0.5% or 1.0% BCD and differing concentrations of niacinamide. The gels were maintained at 5° C. for one week to observe for precipitate or crystal formation. The results are shown in Table 4.

TABLE 4

| BCD % w/w | Niacinamide % w/w | Metronidazole % w/w | Results at 5° C., 1 week |
|---|---|---|---|
| 0.5 | 0.5 | 1.0 | Crystals formed |
| 0.5 | 1.0 | 1.0 | Clear |
| 0.5 | 2.0 | 1.0 | Clear |
| 1.0 | 0.5 | 1.0 | Precipitate formed |
| 1.0 | 1.0 | 1.0 | Clear |
| 1.0 | 2.0 | 1.0 | Clear |

The results in Table 4 show that concentrations of BCD and niacinamide as low as 0.5% and 1.0%, respectively, may be used together to obtain a physically stable aqueous gel solution of 1.0% metronidazole.

EXAMPLE 4

Various gel solutions of Table 1 were prepared with a concentration of 1.0% metronidazole and various concentrations of niacin. The pH was adjusted to 5.0+/−0.15 with trolamine. The solutions were maintained at 5° C. for one week to observe evidence of precipitation or crystal formation. The results are shown in Table 5.

TABLE 5

| Niacin % w/w | MTZ % w/w | Results, 5° C., 1 week |
|---|---|---|
| 2.0 | 1.0 | Clear |
| 1.8 | 1.0 | Clear |
| 1.5 | 1.0 | Clear |
| 1.2 | 1.0 | Clear |
| 1.0 | 1.0 | Clear |
| 0.75 | 1.0 | Clear |
| 0.5 | 1.0 | Clear/Crystals formed* |
| 0.25 | 1.0 | Crystals formed |
| 0.25 | 1.0 | Crystals formed |
| 0.15 | 1.0 | Crystals formed |
| 0.10 | 1.0 | Crystals formed |

*seven out of eight samples showed crystal formation

The results in Table 5 show that the minimum concentration of niacin required to obtain a stable 1.0% metronidazole gel solution is greater than 0.5% and preferably about 0.75%.

EXAMPLE 5

Various solutions according to Table 1 with 1% metronidazole, 0.5% niacin, pH adjusted to 5.0+/−0.15 and varying concentrations of BCD. The solutions were maintained at 5° C. for one week to observe for crystal or precipitate formation. The results are shown in Table 6.

TABLE 6

| BCD % w/w | Niacin % w/w | MTZ % w/w | Results, 5° C., 1 week |
|---|---|---|---|
| 0.2 | 0.5 | 1.0 | Crystals formed |
| 0.3 | 0.5 | 1.0 | Crystals formed |
| 0.5 | 0.5 | 1.0 | Clear |

As shown in Table 6, using a combination of 0.5% niacin and 0.5% BCD, a stable 1.0% aqueous gel solution of metronidazole was produced.

The above data in Examples 1 to 5 show that BCD at its maximum soluble aqueous concentration raises the stable solubility of MTZ in aqueous solution, such as a gel, at 5° C. by 0.1%, that is from 0.7% to 0.8%. A 3% concentration of niacinamide is needed to increase MTZ aqueous solubility by 0.3% to 1%. Thus, niacinamide at about 3% raises the physically stable solubility of MTZ in aqueous gel by an amount that is about 3 times the increase provided by the maximum soluble concentration of BCD.

When BCD and niacinamide are both utilized in the solution, the two compounds act synergistically to increase the solubility of MTZ in water. The data in Examples 1 to 5 show that when BCD is added to an aqueous solution at an amount expected to yield an increase of 0.1% and niacinamide is added at a level that is one third the amount of niacinamide that is able to raise the solubility of MTZ by 0.3%, this combination results in a solubility of MTZ that is 0.3% above its unaided solubility.

Similar results were obtained using a 0.5% concentration of niacin, a concentration which is below that which produces a stable 1% solution of metronidazole. When this concentration of niacin was combined with 0.5% BCD, a concentration that provides only a 0.1% increase in MTZ aqueous solubility to 0.8%, the solubility of MTZ was synergistically increased to 1% at a pH of about 5.

Various modifications of the above described invention will be evident to those skilled in the art. For example, more than one cyclodextrin may be used, such as beta-cyclodextrin and hydroxypropyl-beta-cyclodextrin. Similarly, the second solubility enhancing agent may be a multiplicity of solubility enhancing agents, such as both niacin and niacinamide. It is intended that such modifications are included within the scope of the following claims.

What is claimed is:

1. An aqueous solution that is physically stable for at least one week at 5° C. comprising metronidazole, a first solubility enhancing agent which is betacyclodextrin, and a second solubility enhancing agent which is niacin or niacinamide, wherein in the solution, the concentration of metronidazole is about 1.0% w/w or higher, the concentration of betacyclodextrin is 0.5% w/w or higher, and the concentration of niacinamide or niacin is about 0.5% w/w or higher.

2. The aqueous solution of claim 1 wherein the solubility enhancing agent is niacinamide.

3. The aqueous solution of claim 2 which is a gel.

4. The aqueous solution of claim 1 wherein the solubility enhancing agent is niacin.

5. The aqueous solution of claim 4 which is a gel.

6. The aqueous solution of claim 1 which comprises niacinamide and does not comprise niacin.

7. The aqueous solution of claim 1 wherein the concentration of niacinamide or niacin is about 1.0% w/w or higher.

8. The aqueous solution of claim 7 which comprises niacinamide and does not comprise niacin.

9. The aqueous solution of claim 1 which is a gel.

10. An aqueous solution comprising metronidazole, betacyclodextrin at a concentration of 0.5% w/w or higher, and niacinamide, wherein the solution is free of crystal or precipitate formation when stored for one week at 5° C.

11. The aqueous solution of claim 10 wherein the concentration of betacyclodextrin is about 1% w/w or higher.

12. The aqueous solution of claim 10, which is an aqueous gel solution.

13. A kit for the topical treatment of dermatologic or mucosal disorders comprising a container and an aqueous solution of metronidazole, beta-cyclodextrin, and niacin or niacinamide within said container, wherein the concentration of metronidazole in said solution is higher than 0.75% w/w, the concentration of beta-cyclodextrin is 0.5% w/w or higher, and the concentration of niacin or niacinamide is about 1.0% w/w or higher.

14. The kit of claim 13 wherein the concentration of metronidazole is about 1% w/w or higher.

15. The kit of claim 13 wherein the aqueous solution is a gel.

16. The kit of claim 13 wherein the solution contains niacinamide and is substantially free of niacin.

17. The kit of claim 13 wherein the solution contains niacin and is substantially free of niacinamide.

18. A method for obtaining an aqueous solution containing metronidazole wherein the aqueous solution contains betacyclodextrin at a concentration greater than 0.5% w/w comprising combining in an aqueous fluid metronidazole, betacyclodextrin and niacinamide wherein the amount of the niacinamide combined in the aqueous fluid is sufficient to provide a dissolved concentration of betacyclodextrin greater than 0.5% w/w at a temperature of 5° C.

19. The method of claim 18 wherein the aqueous solution containing betacyclodextrin at a concentration greater than 0.5% w/w and niacinamide is physically stable for one week at 5° C.

20. The method of claim 18 wherein the aqueous solution is an aqueous gel solution.

21. A method for increasing the solubility of metronidazole in aqueous solution comprising combining metronidazole, betacyclodextrin, and niacinamide or niacin in an aqueous fluid, wherein the concentration of betacyclodextrin in the fluid is 0.5% w/w or more and the concentration of niacinamide or niacin in the fluid is about 1.0% or higher.

22. The method of claim 21 wherein the aqueous solution is a gel.

23. The method of claim 21 which comprises combining niacinamide in the fluid.

24. The method of claim 21 which comprises combining niacin in the fluid.

25. The method of claim 21 wherein the solubility of metronidazole is increased to 0.75% w/w or more.

26. The method of claim 25 wherein the solubility of metronidazole is increased to about 1.0% w/w or more.

27. The method of claim 21 wherein the betacyclodextrin and the niacin or niacinamide are dissolved in the aqueous fluid before the metronidazole is combined in the fluid.

28. The method of claim 21 wherein a gelling agent is added to the fluid after the metronidazole, betacyclodextrin, and the niacin or niacinamide are combined in the fluid.

29. A method for increasing the enhancing effect of betacyclodextrin on the solubility of metronidazole in aqueous fluid comprising combining niacin or niacinamide with the betacyclodextrin in the aqueous fluid, wherein the concentration of betacyclodextrin in the fluid is 0.5% or more and the concentration of niacin or niacinamide is about 1.0% w/w or more.

30. The method of claim 29 wherein the niacin or niacinamide is combined in the fluid with the betacyclodextrin and then metronidazole is added to the fluid.

31. The method of claim 29 wherein niacin is combined with the betacyclodextrin in the aqueous fluid.

32. The method of claim 29 wherein niacinamide is combined with the betacyclodextrin in the aqueous fluid.

33. A method for making an aqueous solution of metronidazole greater than 0.75% w/w comprising combining metronidazole, beta-cyclodextrin (BCD), and niacin or niacinamide in an aqueous fluid, wherein the amount of BCD that is combined in the aqueous fluid is sufficient to provide a concentration of BCD in the solution of 0.5% w/w or higher and wherein the aqueous solution is physically stable when stored for one week at 5° C.

34. The method of claim 33 wherein the metronidazole is added to the aqueous fluid after the BCD and the niacin or niacinamide are dissolved in the aqueous fluid.

35. The method of claim 33 which further comprises, after the combination of metronidazole, BCD, and the niacin or niacinamide, adding a gelling agent.

36. An aqueous solution that is made by the method of claim 35.

37. The method of claim 33 wherein niacinamide but not niacin is combined.

38. An aqueous solution that is made by the method of claim 37.

39. The method of claim 33 wherein niacin but not niacinamide is combined.

40. An aqueous solution that is made by the method of claim 39.

41. An aqueous solution that is made by the method of claim 33.

42. The method of claim 33 wherein the betacyclodextrin is crystalline betacyclodextrin.

43. An aqueous solution that is made by the method of claim 42.

44. A method for the treatment of a dermatologic or mucosal disorder comprising topically applying an effective amount of aqueous solution of metronidazole having a concentration higher than 0.75% w/w to the site of the disorder and permitting the metronidazole to treat the disorder, wherein the solution comprises beta-cyclodextrin (BCD) at a concentration of 0.5% w/w or higher and niacin or niacinamide, and wherein the solution is physically stable when stored for one week at 50° C.

45. The method of claim 44, wherein the concentration of metronidazole is about 1% or higher.

46. The method of claim 45 wherein the application is once daily.

47. The method of claim 44 wherein the disorder is rosacea.

48. The method of claim 44 wherein the solution comprises niacin and is substantially free of niacinamide.

49. The method of claim 44 wherein the solution comprises niacinamide and is substantially free of niacin.

50. The method of claim 44 wherein the aqueous solution is a gel.

* * * * *